US011964124B2

(12) United States Patent
Dern et al.

(10) Patent No.: US 11,964,124 B2
(45) Date of Patent: Apr. 23, 2024

(54) SYSTEMS AND METHODS FOR GUIDED RELAY DELIVERY OF MEDICATION

(71) Applicant: CAREFUSION 303, INC., San Diego, CA (US)

(72) Inventors: Jeffrey Dern, Eysins (CH); Samuel Garcia, Madrid (ES)

(73) Assignee: CAREFUSION 303, INC., San Diego, CA (US)

(*) Notice: Subject to any disclaimer, the term of this patent is extended or adjusted under 35 U.S.C. 154(b) by 236 days.

(21) Appl. No.: 17/546,367

(22) Filed: Dec. 9, 2021

(65) Prior Publication Data

US 2022/0096735 A1    Mar. 31, 2022

Related U.S. Application Data

(63) Continuation of application No. 16/342,489, filed as application No. PCT/US2017/056651 on Oct. 13, 2017, now Pat. No. 11,224,689.

(Continued)

(51) Int. Cl.
*A61M 5/14* (2006.01)
*A61M 5/145* (2006.01)
(Continued)

(52) U.S. Cl.
CPC ............ *A61M 5/1408* (2013.01); *A61M 5/14* (2013.01); *A61M 5/1452* (2013.01);
(Continued)

(58) Field of Classification Search
CPC ............ A61M 5/1684; A61M 5/16809; A61M 2205/33; A61M 2205/50;
(Continued)

(56) References Cited

U.S. PATENT DOCUMENTS

| 5,308,320 A | 5/1994 | Safar |
| 2007/0299389 A1* | 12/2007 | Halbert ................. G06Q 40/08 604/131 |
| 2011/0313789 A1 | 12/2011 | Kamen et al. |

FOREIGN PATENT DOCUMENTS

| CN | 2613269 Y | 4/2004 |
| CN | 1887372 A | 1/2007 |

(Continued)

OTHER PUBLICATIONS

Australian Office Action for Application No. 2017346477, dated May 31, 2022, 4 pages.

(Continued)

*Primary Examiner* — Ariana Zimbouski
*Assistant Examiner* — Avery Smale
(74) *Attorney, Agent, or Firm* — Morgan, Lewis & Bockius LLP

(57) ABSTRACT

Guided relay infusion systems and methods are provided. A guided relay infusion system may be a portion of an infusion pump that can simultaneously deliver a medical fluid from two syringes. When a first one of the syringes is running out of the medical fluid and a second one of the syringes is more full of the medical fluid than the first one of the syringes, guided relay messages are provided for a relay handoff from the first one of the syringes to the second one of the syringes that ensures a smooth continuous delivery of more of the medical fluid than the first one of the syringes holds.

20 Claims, 20 Drawing Sheets

Related U.S. Application Data

(60) Provisional application No. 62/409,316, filed on Oct. 17, 2016.

(51) Int. Cl.
*A61M 5/168* (2006.01)
*G16H 20/17* (2018.01)
*G16H 40/63* (2018.01)

(52) U.S. Cl.
CPC .... *A61M 5/16809* (2013.01); *A61M 5/16827* (2013.01); *A61M 5/16831* (2013.01); *A61M 5/1684* (2013.01); *G16H 20/17* (2018.01); *G16H 40/63* (2018.01); *A61M 2205/18* (2013.01); *A61M 2205/33* (2013.01); *A61M 2205/3334* (2013.01); *A61M 2205/50* (2013.01); *A61M 2205/502* (2013.01)

(58) Field of Classification Search
CPC ...... A61M 2205/3334; A61M 2205/18; A61M 2205/502; A61M 5/1408; A61M 5/1723; A61M 5/14; A61M 5/16831; A61M 5/1452; A61M 5/16827; A61M 5/1407; A61M 5/145; A61M 5/1456; A61M 2005/1787; A61M 5/14566; A61M 2005/14573; A61M 5/172; A61M 5/1726; A61M 2205/123; A61M 2230/30; A61M 2230/00; A61M 2230/202; G16H 20/17
See application file for complete search history.

(56) References Cited

FOREIGN PATENT DOCUMENTS

| | | | | |
|---|---|---|---|---|
| CN | 101111281 | A | 1/2008 | |
| CN | 201658699 | U | 12/2010 | |
| CN | 102014988 | A | 4/2011 | |
| CN | 102114278 | A | 7/2011 | |
| CN | 103153361 | A | 6/2013 | |
| CN | 103705998 | A | 4/2014 | |
| CN | 204542392 | U | 8/2015 | |
| CN | 205145293 | U | 4/2016 | |
| CN | 105616167 | A | 6/2016 | |
| CN | 205494543 | U | 8/2016 | |
| EP | 2623141 | A1 * | 8/2013 | .......... A61M 5/1413 |
| JP | 2001333978 | A | 12/2001 | |
| JP | 2012090965 | A | 5/2012 | |
| JP | 2013192890 | A | 9/2013 | |
| WO | WO-2010090669 | A1 | 8/2010 | |
| WO | WO-2011133724 | A2 | 10/2011 | |
| WO | WO-2013043881 | A1 | 3/2013 | |
| WO | WO-2013096713 | A2 | 6/2013 | |
| WO | WO-2015123012 | | 8/2015 | |
| WO | WO-2016152294 | | 9/2016 | |

OTHER PUBLICATIONS

United Arab Emirates Office Action for Application No. P6000545/2019, dated Feb. 21, 2023, 12 pages.
Brazilian Office Action for Application No. BR112019005692-0, dated Jan. 7, 2022, 5 pages including translation.
Chinese Office Action for Application No. 201780063593.8, dated Apr. 13, 2021, 24 pages including translation.
Chinese Office Action for Application No. 201780063593.8, dated Aug. 16, 2021, 4 pages including translation.
Chinese Office Action for Application No. 201780063593.8, dated Oct. 28, 2020, 18 pages.
Colombia Office Action for Application No. NC2019/0003873, dated Apr. 29, 2021, 27 pages including machine translation.
International Search Report and Written Opinion for Application No. PCT/US2017/056651, dated Jan. 31, 2018, 11 pages.
Japanese Office Action for Application No. 2019-520558, dated Feb. 10, 2022, 4 pages including translation.
Japanese Office Action for Application No. 2019-520558, dated Jul. 2, 2021, 7 pages including translation.

* cited by examiner

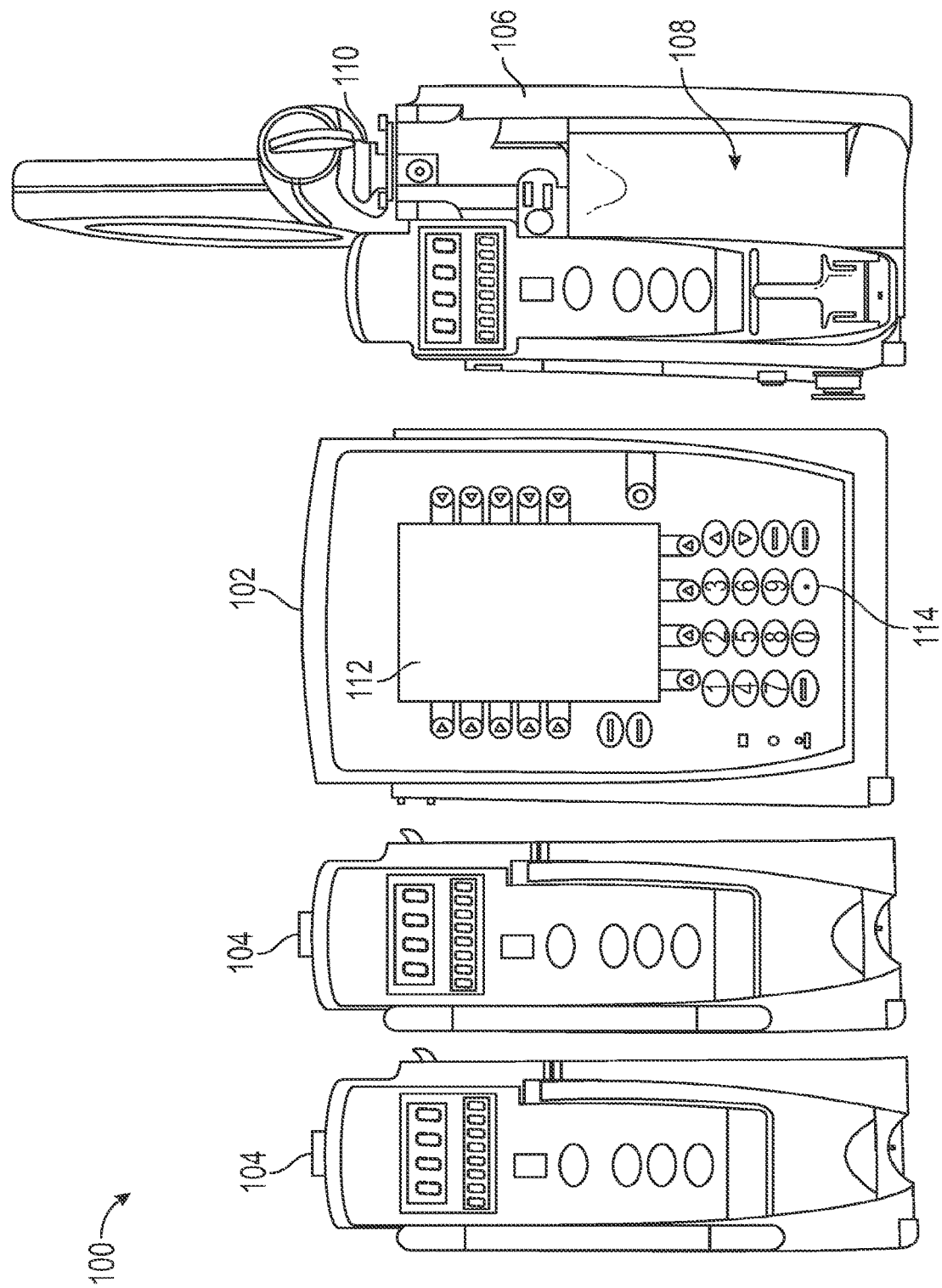

FIG. 6D

| | | | | | | | | | |
|---|---|---|---|---|---|---|---|---|---|
| | | | | | | | | | |
| | | | | | | | | | |
| | | | | | | | | | |
| | | | | | | | | | |
| | | | | | | | | | |
| ⊙ Propofol 1%<br>10mg/ml<br>☐ Pressure | | 2.5 mL/h<br>5.21 mL | | | | | | | |
| Insulin<br>1U/mL<br>☐ Pressure 0 mm Hg | | 2 mL/h<br>3.67 mL | | | | | | | |
| DOPamine ☆®<br>4mg/ml<br>☐ Pressure 0 mm Hg | | 2 mL/h<br>1.51 mL | | | | | | | |
| DOPamine ☆®<br>4mg/ml<br>☐ Pressure 0 mm Hg | | 0 mL/h<br>mL | | | | | | | |

Guided Relay Message: 15 Minutes to Next Rate Change. Next Rate Change will change the emptying syringe to 1 mL and the relay syringe to 1mL.

[File] [Edit] [View] [Tools] [Window] [Help]   [↓] [↑]

FIG. 6E

| | | | | | | | |
|---|---|---|---|---|---|---|---|
| ⊙Propofol 1% | | | | 2.5 mL/h | | | |
| 10mg/ml | | | | 5.21 mL | | | |
| ☐Pressure | | | | | | | |
| Insulin | | | | 2 mL/h | | | |
| 1U/mL | | | | 3.67 mL | | | |
| ☐Pressure 0 mm Hg | | | | | | | |
| DOPamine☆℞ | | | | 2 mL/h | | | |
| 4mg/ml | | | | 1.51 mL | | | |
| ☐Pressure 0 mm Hg | | | | | | | |
| DOPamine☆℞ | | | | 0 mL/h | | | |
| 4mg/ml | | | | mL | | | |
| ☐Pressure 0 mm Hg | | | | | | | |

Guided Relay Message: Within window to make a Rate Change. Please change the emptying syringe to 0.5 mL and the realy syringe to 1.5 mL.

[File] [Edit] [View] [Tools] [Window] [Help]   [↓] [↑]

| | | | | | | | |
|---|---|---|---|---|---|---|---|
| | | | | | | | |
| | | | | | | | |
| | | | | | | | |
| | | | | | | | |
| ⊙Propofol 1% | | 2.5 mL/h | | | | | |
| 10mg/ml | | 5.21 mL | | | | | |
| ☐Pressure | | | | | | | |
| Insulin | | 2 mL/h | | | | | |
| 1U/mL | | 3.67 mL | | | | | |
| ☐Pressure 0 mm Hg | | | | | | | |
| DOPamine ☆ | | 2 mL/h | | | | | |
| 4mg/ml | | 1.51 mL | | | | | |
| ☐Pressure 0 mm Hg | | | | | | | |
| DOPamine ☆ | | 0 mL/h | | | | | |
| 4mg/ml | | mL | | | | | |
| ☐Pressure 0 mm Hg | | | | | | | |

Guided Relay Message: 15 Minutes to Next Rate Change. Next Rate Change will change the emptying syringe to .5mL and the relay syringe to 1.5mL. ⟵ 722

[File] [Edit] [View] [Tools] [Window] [Help]   [↓] [↑]

FIG. 6J

| | | | | | | | |
|---|---|---|---|---|---|---|---|
| ⊙Propofol 1% | | | | | 2.5 mL/h | | |
| 10mg/ml | | | | | 5.21 mL | | |
| ☐Pressure | | | | | | | |
| Insulin | | | | | 2 mL/h | | |
| 1U/mL | | | | | 3.67 mL | | |
| ☐Pressure 0 mm Hg | | | | | | | |
| DOPamine ☆℞ | | | | | 2 mL/h | | |
| 4mg/ml | | | | | 1.51 mL | | |
| ☐Pressure 0 mm Hg | | | | | | | |
| DOPamine ☆℞ | | | | | 0 mL/h | | |
| 4mg/ml | | | | | mL | | |
| ☐Pressure 0 mm Hg | | | | | | | |

Guided Relay Message: Within window to make a Rate Change. Please change the emptying syringe to 0.5mL and the relay syringe to 1.5mL. — 724

[File] [Edit] [View] [Tools] [Window] [Help]   [↓] [↑]

| | | | | | | | |
|---|---|---|---|---|---|---|---|
| ⊙Propofol 1% | | | | | | 2.5 mL/h | |
| 10mg/ml | | | | | | 5.21 mL | |
| ☐Pressure | | | | | | | |
| Insulin | | | | | | 2 mL/h | |
| 1U/mL | | | | | | 3.67 mL | |
| ☐Pressure 0 mm Hg | | | | | | | |
| DOPamine ☆® | | | | | | 2 mL/h | |
| 4mg/ml | | | | | | 1.51 mL | |
| ☐Pressure 0 mm Hg | | | | | | | |
| DOPamine ☆® | | | | | | 0 mL/h | |
| 4mg/ml | | | | | | mL | |
| ☐Pressure 0 mm Hg | | | | | | | |

Guided Relay Message: Within window to make a Rate Change. Please change the emptying syringe to 0.0 mL and the relay syringe to 2.0 mL. —728

[File] [Edit] [View] [Tools] [Window] [Help]  [↓] [↑]

'Guided Relay' is complete.
Send syringe transition
information to PDMS?
Yes    No - Keep it Separate Propofol 1%
10mg/ml
Pressure
2.5 mL/h
5.21 mL Insulin
1U/mL
Pressure 0 mm Hg
DOPamine
4mg/ml
Pressure 0 mm Hg
DOPamine
4mg/ml
Pressure 0 mm Hg
1.51 mL
0 mL/h
mL File  Edit  View  Tools  Window  Help

SYSTEMS AND METHODS FOR GUIDED RELAY DELIVERY OF MEDICATION

CROSS-REFERENCE TO RELATED APPLICATIONS

This application is a continuation of U.S. patent application Ser. No. 16/342,489, filed Apr. 16, 2019, issued as U.S. Pat. No. 11,224,689 on Jan. 18, 2022, which is a U.S. National Stage Entry of International Application No. PCT/US2017/056651, filed on Oct. 13, 2017, which claims the benefit of U.S. Provisional Patent Application No. 62/409,316, filed on Oct. 17, 2016, the entire contents of which are incorporated by reference herein.

TECHNICAL FIELD

The present disclosure generally relates to the administration of medical fluids and, in particular, relates to systems and methods for multiple syringe delivery of medical fluids.

BACKGROUND

Medical fluids are often delivered to a patient via a syringe. However, in some scenarios, delivery of a medical fluid from a single syringe can be problematic.

SUMMARY

Aspects of the subject technology relate to systems and methods of guided relay of infusion from one container source to another container source for the same medication.

In accordance with certain aspects, a system is provided that includes a first actuable component configured to couple to a plunger of a first syringe containing a medication, a second actuable component configured to couple to a plunger of a second syringe containing the same medication, a display, and a processor. The processor is configured to operate the first actuable component to move the plunger of the first syringe at a first rate, operate the second actuable component to move the plunger of the second syringe at a second rate while operating the first actuable component at the first rate, and operate the display to provide a message that describes a decrease in the first rate and a corresponding increase in the second rate.

In accordance with certain aspects, a computer-implemented method is provided that includes operating a first syringe to administer a medical fluid from the first syringe, detecting a second syringe, and providing one or more guided relay messages to a user for transitioning from administering the medical fluid from the first syringe to administering the medical fluid from the second syringe.

In accordance with certain aspects, an infusion pump having processing circuitry and non-transitory machine-readable media is provided, the non-transitory machine-readable media storing instructions that, when executed by the processing circuitry cause the processing circuitry to operate a first syringe that is coupled to the infusion pump to move a medical fluid from the first syringe into infusion tubing, detect a second syringe coupled to the infusion pump, and provide one or more guided relay messages on a display of the infusion pump for transitioning from administering the medical fluid from the first syringe to administering the medical fluid from the second syringe.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 1A is a diagram illustrating a system for administering medical fluid to a patient using multiple syringes according to certain aspects of the present disclosure.

DETAILED DESCRIPTION

Figure 1B:
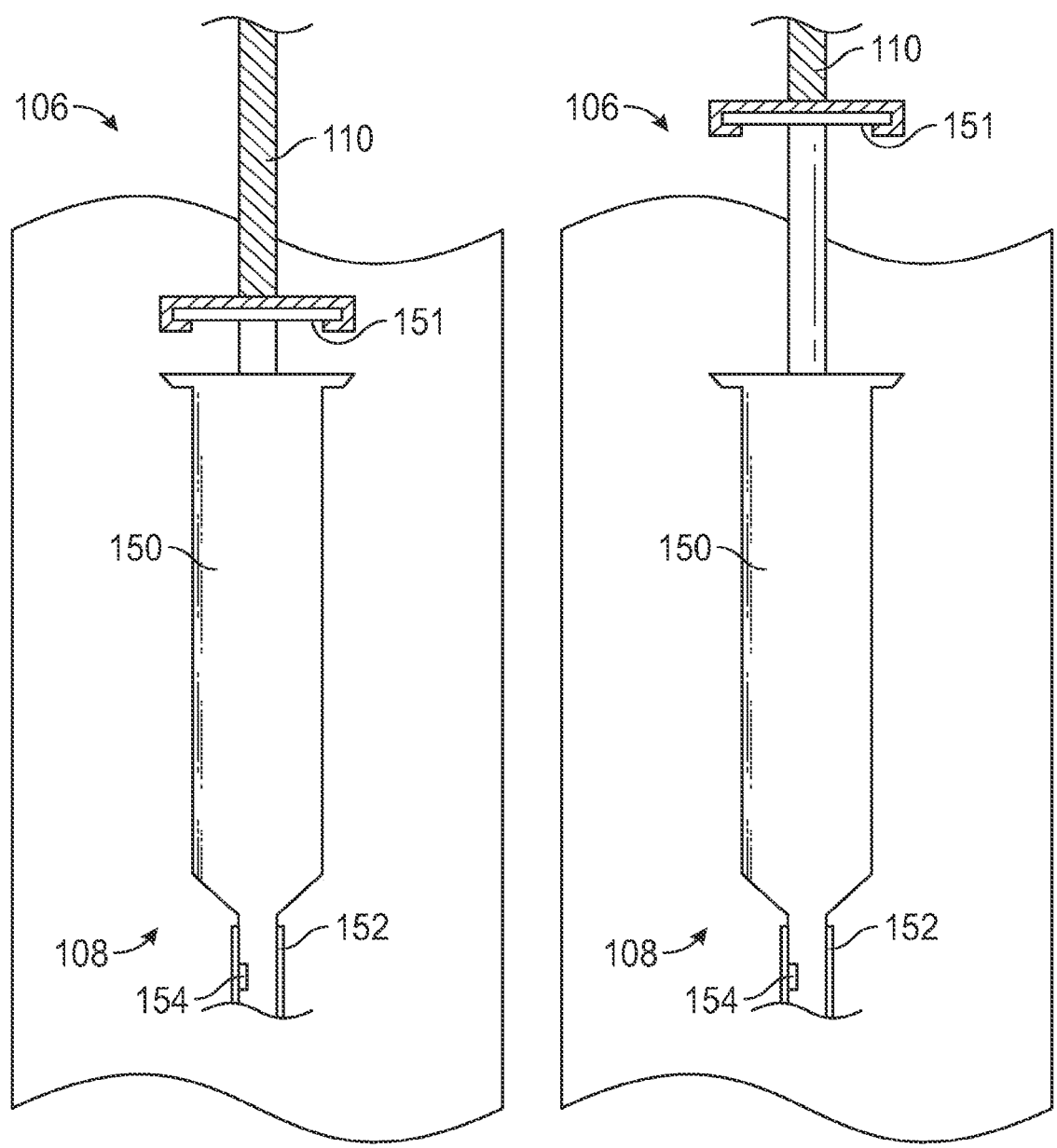
FIG. 1B is a diagram illustrating multiple syringes for delivering a medical fluid according to certain aspects of the present disclosure.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

Medical fluids such as inotropes may be provided to a patient from one or more syringes. Inotropes may be provided over a period of time such as a 24 hour period from one syringe. However, in some scenarios, a syringe for delivery of a medical fluid such as an inotrope may need to be changed more frequently than the time for a delivery of a complete dose, for example, depending on a patient condition. Medical fluids such as inotropes also have a short (e.g., 2 minute) half-life and the wrong concentration of these drugs in the body can cause negative and/or dangerous effects for a patient. Accordingly, a new syringe containing relatively a newer inotrope than a current syringe from which the inotrope is being administered may be needed during continuous administration of the inotrope. Example inotrope drugs include DOPamine, DOBUtamine, NORadrenalin, and Fusoemide.

In accordance with some aspects, systems and methods may be provided for guided relay of medical fluid administration from multiple syringes. For example, a first syringe may be provided from which a medical fluid is administered to a patient (e.g., as controlled by an infusion pump) for a first period of time. A second syringe may be provided from which the medical fluid is administered during a second period of time after the first period of time. During a transition period between the first and second periods of time, a combined administration of the medical fluid may be provided from the first and second syringes. During the transition period, the administration of the medical fluids may be relayed from the first syringe to the second syringe by slowing the delivery rate of the first syringe while simultaneously increasing the delivery rate of the second syringe to maintain a constant overall delivery rate. Various guided relay messages such as guiding alerts and notifications may be provided (e.g., by the infusion pump and/or other monitoring equipment) to prevent patient hazards that may occur during such a relay transition, as described in further detail hereinafter.

In accordance with some aspects, systems and methods for guided relay of medical fluid administration as disclosed herein may help ensure that a clinician can transition their patients from a current syringe to new syringe with drug delivery continuity and with minimal increases to workload. Systems and methods for guided relay of medical fluid administration as disclosed herein may help establish a combined dose and delivery rate from multiple syringes at a desired delivery rate for the patient and monitor and guide a clinician such as a nurse to maintain the established dose and delivery rate at the desired dose and delivery rate for a consistent end patient effect over the course of (e.g., inotrope) syringe transition.

In accordance with some aspects, systems and methods for guided relay of medical fluid administration as disclosed herein may help prevent patient errors by, for example: (i) monitoring the total combined fluid rate of two or more syringes to ensure the total combined fluid rate continuously meets the appropriate target levels for delivery to the patient, (ii) displaying one or more reminders of upcoming and/or past due steps for the syringe transition, the reminders being visible at the bedside and remotely in some embodiments, and (iii) providing combined infusion data to a patient data management system (PDMS) in order to allow easier documentation of the infusion.

In accordance with some aspects, systems and methods for guided relay of medical fluid administration as disclosed herein may help prevent patient hazards such as (A) a patient crashing due to inconsistent medication in their blood stream, potentially caused by a non-therapeutic combined rate from multiple syringes, (B) a clinician such as a nurse missing a syringe transition window causing a first syringe to go empty, and/or (C) documentation errors due to the combined infusion being a sum of two pump modules associated with the two syringes.

In accordance with some aspects, monitoring the total combined fluid rate of two or more syringes to ensure the total combined fluid rate continuously meets the appropriate levels for delivery to the patient may help prevent medication errors associated with hazard A described above. In accordance with some aspects, displaying one or more reminders of upcoming and/or past due steps for the syringe transition may help prevent medication errors associated with hazard B described above. In accordance with some aspects, providing combined infusion data to a patient data management system (PDMS) in order to allow easier documentation of the infusion may help prevent medication errors associated with hazard C described above.

In some embodiments, guided relay systems may provide notifications to one or more vital signs monitoring systems that a syringe transition is occurring or is about to occur. The guided relay system and/or the vital signs monitoring system may provide relatively tighter vital signs limits for the vital signs monitoring systems during the transition. In accordance with some aspects, providing notifications to one or more vital signs monitoring systems that a syringe transition is occurring or is about to occur may help prevent medication errors associated with one or more of hazards A, B, and C described above.

In some embodiments, guided relay systems may include one or more sensors disposed at one or more locations within infusion lines to measure actual flow rates within or between different segments of infusion lines. Flow rates may be displayed to a clinician such as a nurse for monitoring of the transition. In accordance with some aspects, providing one or more sensors disposed at one or more locations within infusion lines to measure actual flow rates within or between different segments of infusion lines may help prevent medication errors associated with one or more of hazards A, B, and C described above.

In some embodiments, guided relay systems may receive patient condition information such as vital signs information from a vital signs monitoring system and may dynamically adjust the period during which flow from one or more medication syringes will be controlled based upon the patient condition information. In accordance with some aspects, dynamically adjusting the period during which flow from one or more medication syringes will be controlled based upon the patient condition information may help prevent medication errors associated with one or more of hazards A, B, and C described above.

In some embodiments, guided relay systems may provide remote control access for remote adjustment of an infusion rate (e.g., back to a safer setting) depending upon vital signs readings from the patient (e.g., from a vital signs monitoring system). In accordance with some aspects, providing remote control access for remote adjustment of an infusion rate (e.g., back to a safer setting) depending upon vital signs readings from the patient (e.g., from a vital signs monitoring system) may help prevent medication errors associated with one or more of hazards A, B, and C described above.

Turning now to the drawings, FIG. 1A shows an exemplary a system 100 for administration of medical fluids. As shown in FIG. 1A, system 100 may include infusion pump 102 and one or more pump modules such as pump modules 104 for controlling administration of medical fluids from intravenous (IV) bags by manipulation of tubing coupled to the IV bags and syringe module 106. One or more pump modules 104, syringe modules 106, and/or other modules such as vital signs monitoring modules (e.g., blood pressure, heart rate, oxygen saturation (Spo2), partial pressure or maximal concentration of carbon dioxide (EtCo2), or other vital signs monitors) or identification modules (e.g., scanning modules for capturing a patient identifier (ID), a clinician ID and/or drug information) may be coupled to and/or operated by infusion pump 102.

Although only one syringe module 106 is shown in FIG. 1A, two, three, or more than three syringe modules may be coupled to and/or operated by infusion pump 102. For example, infusion pump 102 may include processing circuitry (e.g., one or more central processing units or dedicated processor modules) and non-transitory machine-readable media (e.g., volatile or non-volatile memory including permanent and/or removable memory). The non-transitory machine-readable media may store sequences of instructions or code that, when executed by the processing circuitry causes the processing circuitry to operate one or more of pump modules 104, syringe module 106, and/or other modules or components (e.g., display 112, input/output components 114, and/or communications circuitry for communications with other systems or devices). The non-transitory machine-readable media may store sequences of instructions or code that, when executed by the processing circuitry causes the processing circuitry to perform a guided relay process for transitioning delivery of a medical fluid from a first syringe in a first syringe module 106 to delivery of the medical fluid from a second syringe in a second syringe module 106. In this way, a guided relay system may be incorporated within an infusion pump system.

Infusion pump 102 may operate multiple syringe modules 106 to control delivery of a medical fluid from multiple syringes, each disposed in a respective syringe recess 108 of a corresponding syringe module (e.g., by controllably depressing a plunger of the syringe by moving an actuable component such as actuating platform 110). FIG. 1B shows two exemplary syringes 150, each disposed in a corresponding syringe recess 108 of a respective syringe module 106.

As shown in FIG. 1B, a plunger 151 of each syringe 150 is mechanically coupled to actuable component 110 of the syringe module so that pump 102 can actuate the plunger to control the flow of a medical fluid from the syringe to medical tubing 152 (e.g., infusion tubing). The medical tubing may be coupled to a patient receiving the medical fluid intravenously. As shown in FIG. 1B, sensors 154 such as flow sensors may be disposed in the medical tubing for sensing a flow rate of the medical fluid in the tubing (e.g., for monitoring, such as by pump 102, of the individual flow rates from syringes 150 and/or the overall flow rate from both syringes). It should also be appreciated that the individual flow rates from syringes 150 and/or the overall flow rate from both syringes can also, or alternatively, be monitored by monitoring the motion of actuating members 110 for known syringe sizes and volumes. As described in further detail hereinafter, one or more alerts may be generated based on a measured flow rate as obtained using one or more of sensors 154.

Although the guided relay processes described herein are sometimes described as being performed by an infusion pump 102 coupled to the syringe module, it should be appreciated that in other embodiments, guided relay processes may be performed entirely, or in part, by other systems separate from the infusion pump system such as by a standalone guided relay system that is communicatively coupled to infusion pump 102.

Figure 2:
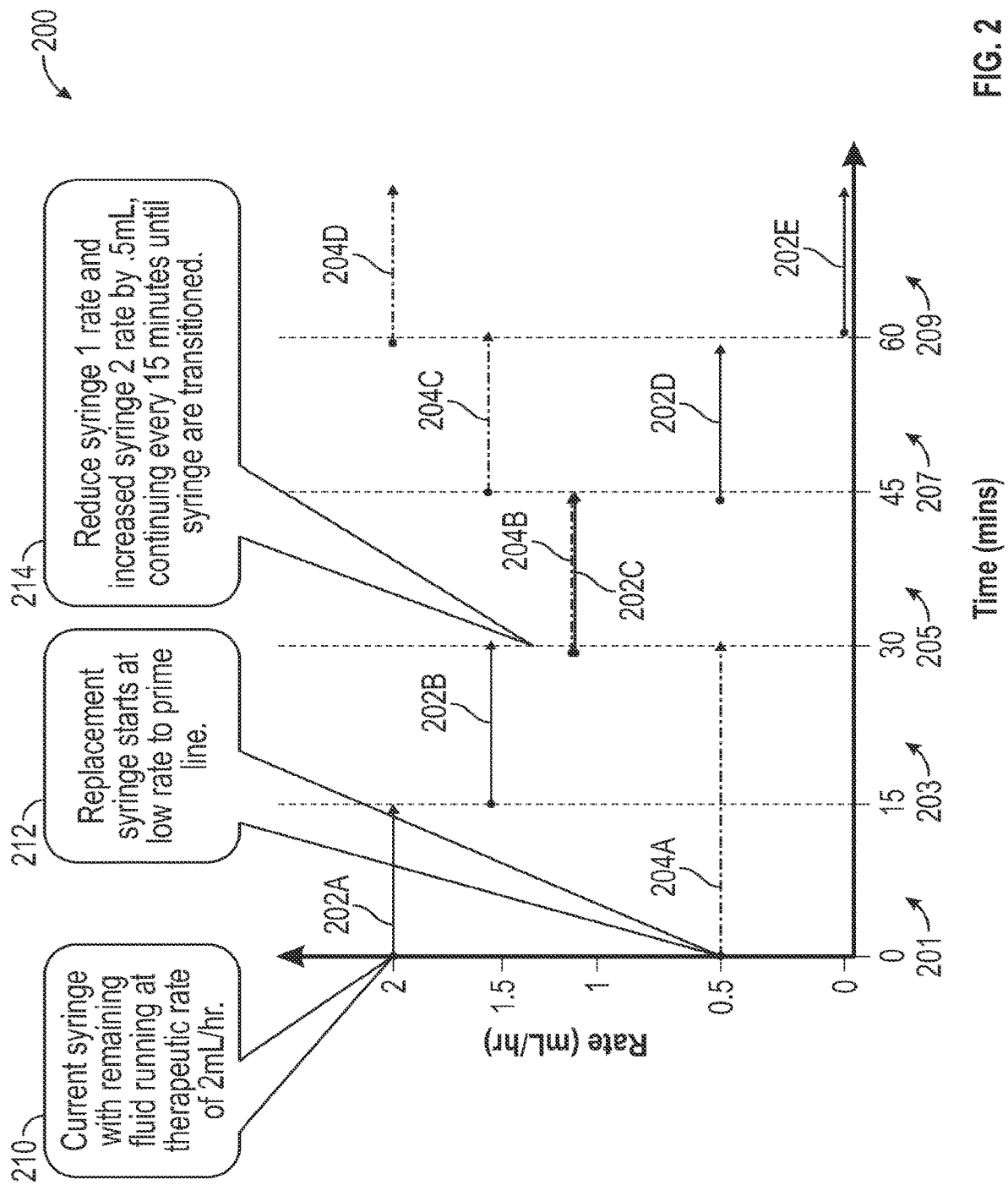
FIG. 2 illustrates exemplary flow rates over time during administration of a medical fluid from two syringes according to certain aspects of the present disclosure.

FIG. 2 shows a flow diagram illustrative exemplary flow rates during a transition period 200 during which administration of a medical fluid from a first syringe is relayed or "handed off" smoothly to a second syringe. As shown in FIG. 2, at block 210 during a first period of time 201, a first or current syringe 152 with remaining medical fluid may be running (e.g., being operated by depressing plunger 151 of the first syringe with a first member 110) to deliver the medical fluid at therapeutic rate 202A of, for example, 2 mL/hr. During first period of time 201, at block 212 a second or replacement syringe 150 starts running (e.g., being operated by depressing plunger 151 of the second syringe with a second member 110) to deliver the same medical fluid at a priming rate 204A (e.g., 0.5 mL/hr) (e.g., to prime a secondary infusion line 154 from the second syringe).

During a second period of time 203 (e.g., after the secondary line has been primed), at block 214 the replacement syringe may continue to run at the priming rate 204A while the current syringe delivery rate is reduced (e.g., automatically or by a clinician such as a nurse) to a relatively lower rate 202B (e.g., 1.5 mL/hr) to accommodate delivery of the medical fluid at the priming rate from the replacement syringe.

Following second period of time 203, the delivery rate from the first syringe may be decreased and the delivery rate from the second syringe may be correspondingly increased (e.g., in 0.5 mL/hr increments), until delivery of the medical fluid is transitioned from the first syringe delivery to the second syringe delivery. For example, during a third period of time 205, delivery from the first syringe may be provided at a rate 202C (e.g., 1 ml/hr) that is equal to the delivery rate 204B from the second syringe. During a fourth period of time 207, delivery from the first syringe may be reduced to a rate 202D (e.g., 0.5 mL/hr) and the delivery from the second syringe may be correspondingly increased to a delivery rate 204C (e.g., 1.5 ml/hr). During a fifth period of time 209, delivery from the first syringe may be reduced to a rate 202E (e.g., delivery from the first syringe may be stopped by reducing delivery to a rate of 0 ml/hr) and the delivery from the second syringe may be correspondingly increased to a delivery rate 204D (e.g., 2.0 ml/hr) equal to the therapeutic rate to complete the transition and takeover of delivery by the second syringe. The delivery from the first syringe may be stopped before all of the fluid in the first syringe has been delivered to ensure a smooth transition and consistent takeover by the second syringe.

Figure 3:
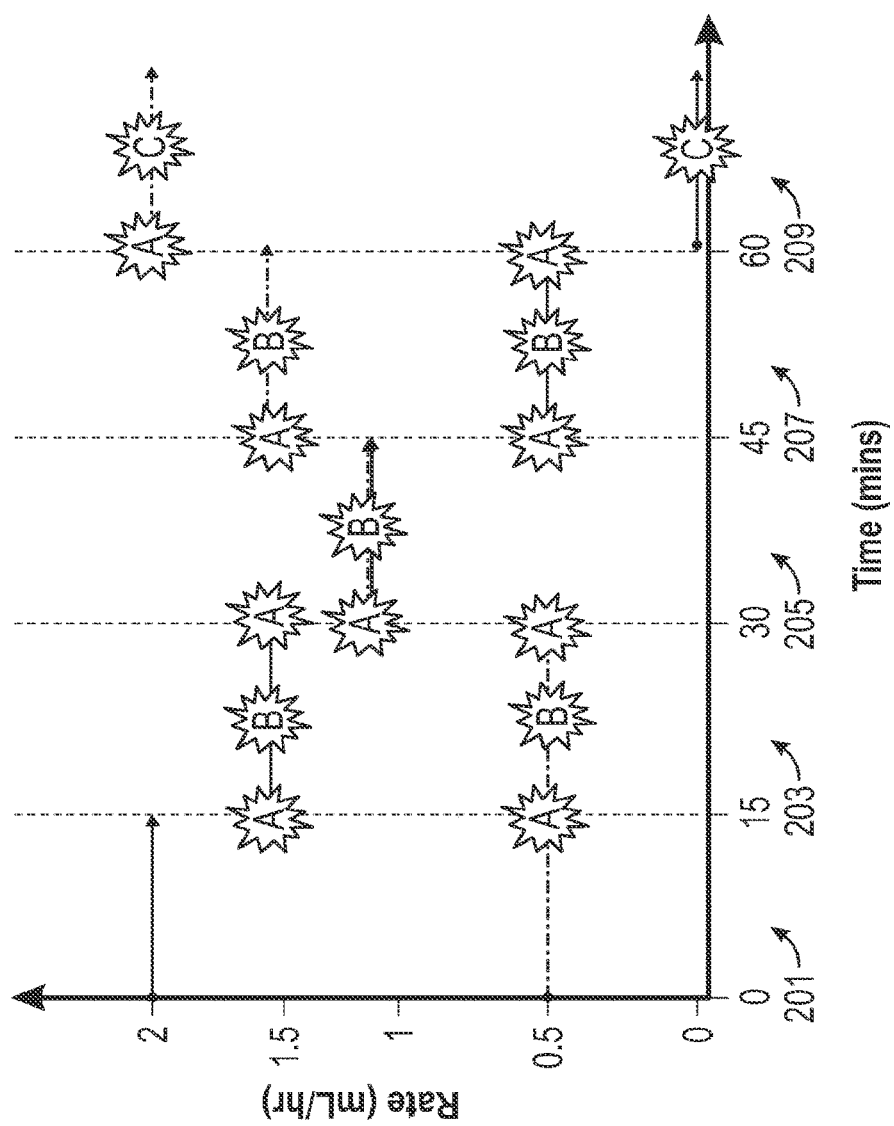
FIG. 3 illustrates various exemplary patient hazards during administration of a medical fluid from two syringes according to certain aspects of the present disclosure.

FIG. 3 shows the chart of FIG. 2 with indicators corresponding to various times during transition period 200 at which one or more of the patient hazards A, B, and C (described above) may occur without the use of a guided relay system as described herein.

Figure 4:
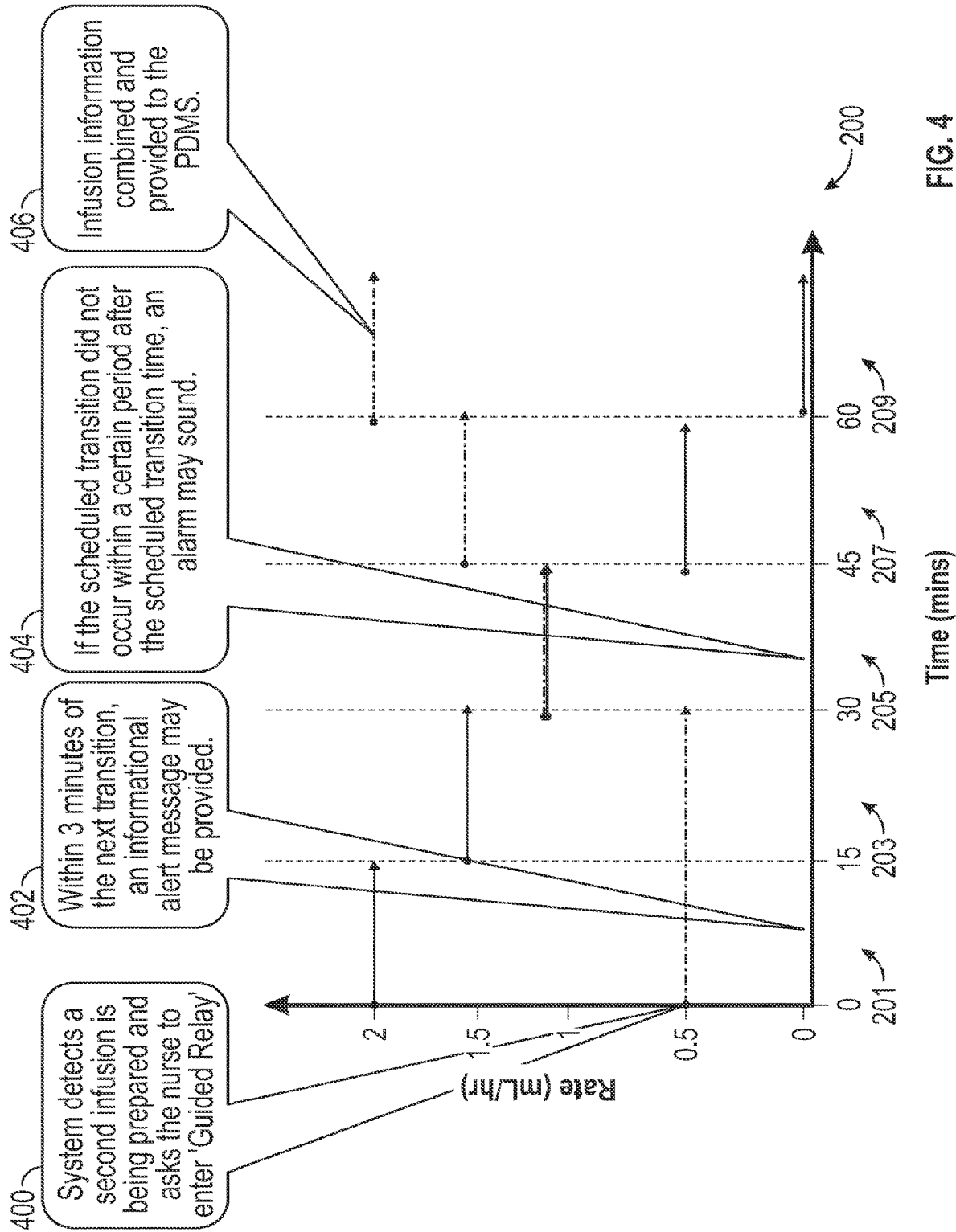
FIG. 4 illustrates exemplary flow rates over time during guided relay administration of a medical fluid from two syringes according to certain aspects of the present disclosure.

FIG. 4 shows a flow diagram of various operations that may be performed for guided relay, overlaid on the chart of FIG. 2. As shown in the example of FIG. 4, at block 400, a system such as a guided relay system for an infusion pump detects a second infusion (e.g., a second syringe when a first syringe is being operated to deliver a medical fluid) is being prepared and asks the nurse to enter a "Guided Relay" mode (e.g., by providing a prompt on display 112). At block 402, within, for example, three minutes of the next transition of the flow rates, an informational alert message may be provided by the guided relay system (e.g., an alert message may be displayed or flash on a display of the system such as display 112 of FIG. 1). At block 404, if it is determined by the guided relay system (e.g., based on sensors in the syringe recesses, based on actuation of syringe plungers or based on sensor information from within the infusion lines) that the scheduled transition did not occur within a certain period (e.g., three minutes) after the scheduled transition time, an alarm may sound (e.g., using a speaker of the infusion pump). At block 406, infusion information may be combined and provided to the PDMS by the guided relay system.

Figure 5:
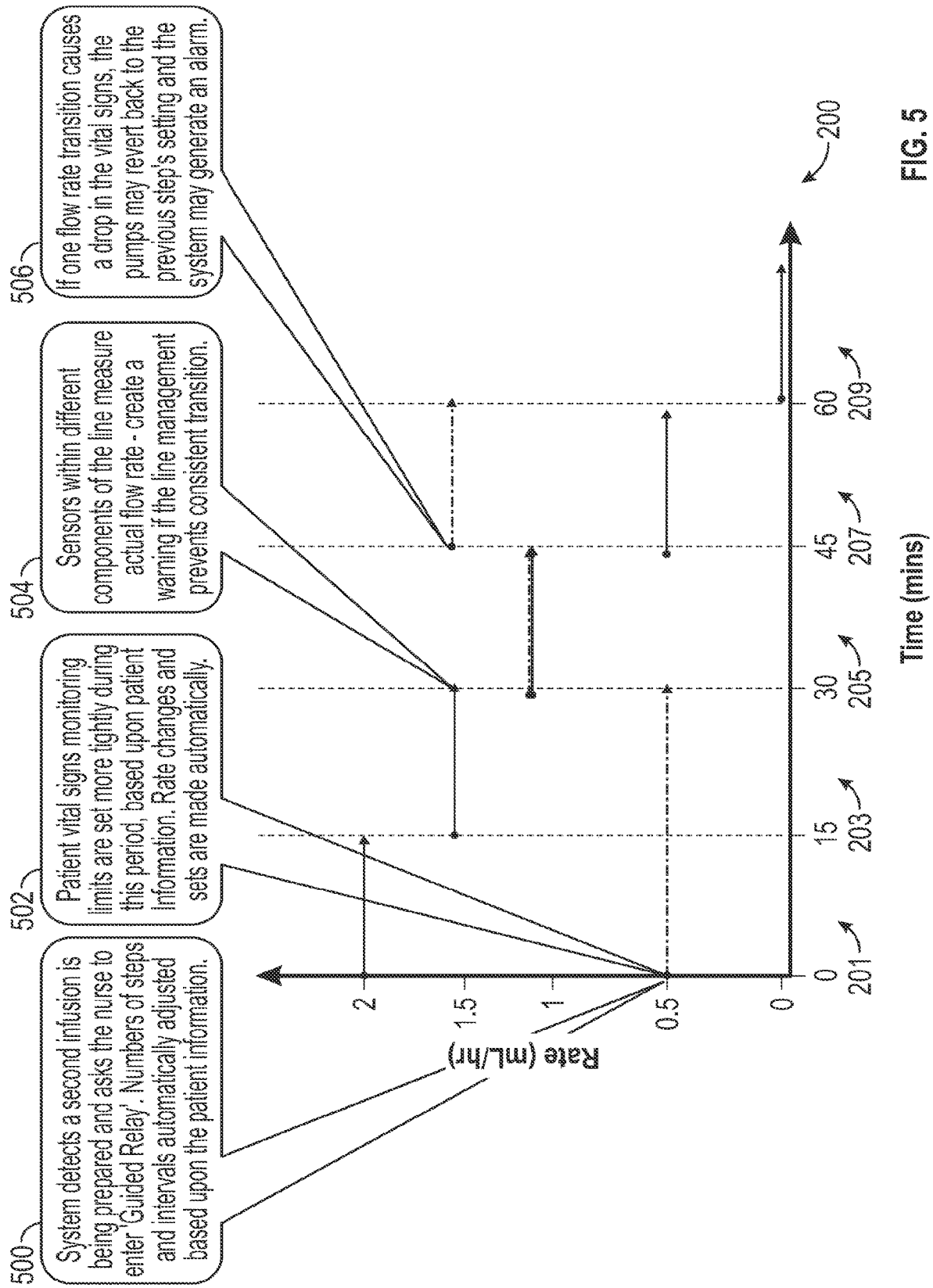
FIG. 5 illustrates additional features of exemplary flow rates over time during guided relay administration of a medical fluid from two syringes according to certain aspects of the present disclosure.

FIG. 5 shows another flow diagram of various operations that may be performed for guided relay overlaid, on the chart of FIG. 2. As shown in the example of FIG. 5, at block 500, a system such as a guided relay system for an infusion pump detects a second infusion (e.g., a second syringe when a first syringe is being operated to deliver a medical fluid) is being prepared and asks the nurse to enter a "Guided Relay" mode. Numbers of steps and intervals for the guided relay may be automatically adjusted by the system based upon patient information. At block 502, patient vital signs monitoring limits may be set more tightly during transition period 200. For example, acceptable limits on patient blood pressure, blood oxygen content, heart rate, etc. may be modified so that changes in the patient vital signs that may be caused by changes in the infusion can be quickly detected and addressed (e.g., by returning to a previous infusion state). At block 504, one or more sensors within different components of the line (e.g., one or more sensors within infusion tubing associated with an individual syringe and/or one or more sensors within tubing that receives medical fluid from both syringes) may provide signals for measuring the actual flow rate therein. Signals from the sensors may be used to generate a warning if the line management prevents consistent transition. At block 506, if one flow rate transition causes a drop in the vital signs (e.g., a drop that violates one of the tightened limits), the pumps may revert back to the previous step's flow rate settings and the system may generate an alarm or alert. Any or all of the operations described in connection with FIG. 5 may be performed separately or together with and/or all of the operations described in connection with FIG. 4.

Figure 6A:
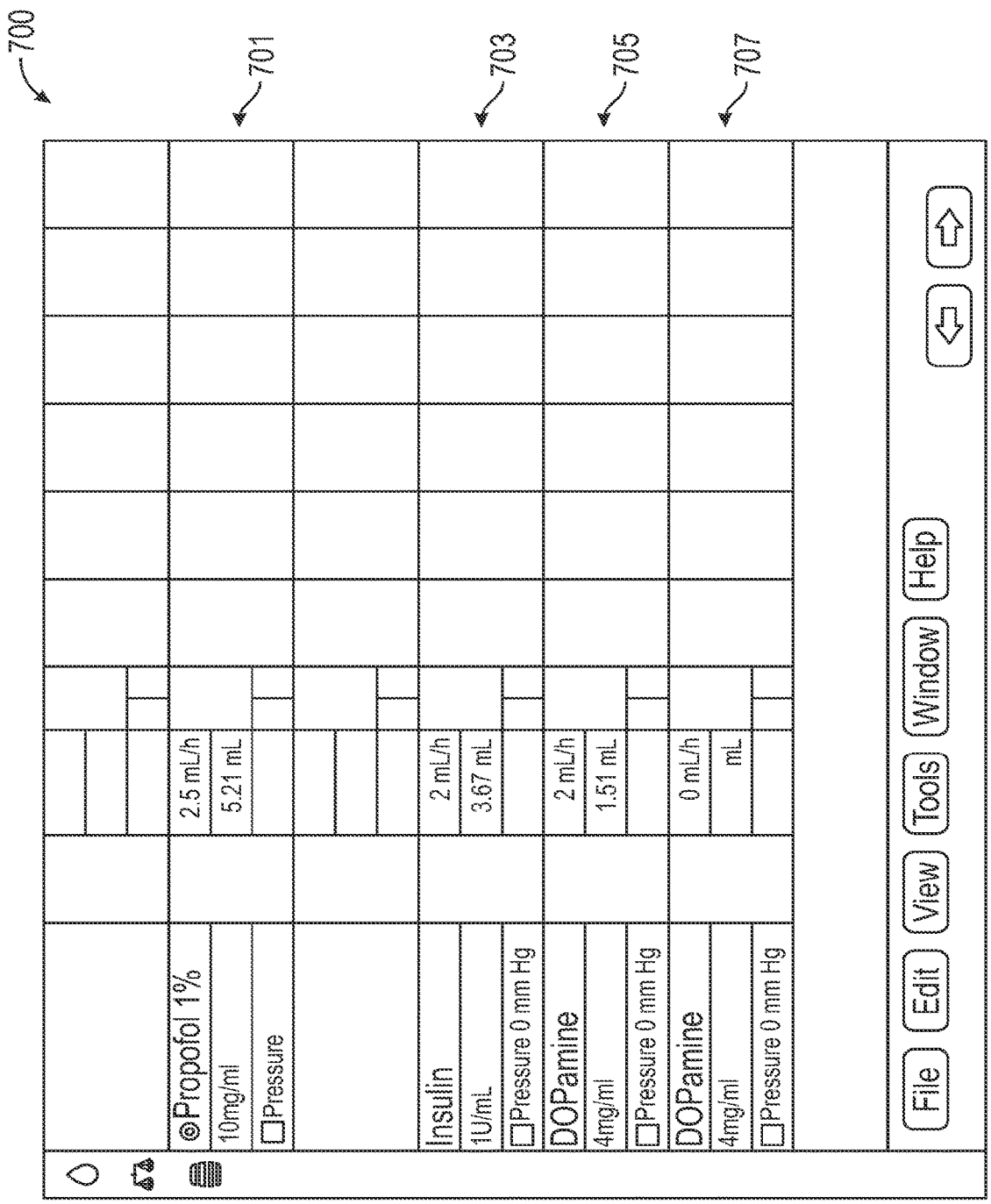
FIGS. 6A-6N illustrate display screen examples that may be displayed at various stages during an exemplary process for guided relay administration of a medical fluid from two syringes according to certain aspects of the present disclosure.

FIG. 6A shows an exemplary display screen 700 generated by a guided relay system such as system 100 of FIG. 1. For example, display screen 700 may be displayed using display 112 of FIG. 1 in some implementations. In the example of FIG. 6A, display screen 700 shows monitoring information 701 for a first drug (e.g., Propofol 1%) with a first pump and monitoring information 703, 705, and 707 respectively for infusions of insulin, Dopamine, and Dopamine with a second pump. For example, a first 50 mL syringe of DOPamine may be infusing at a flow rate of 2 mL/hr by a first syringe module and a clinician may prepare a replacement syringe of DOPamine and load the replacement syringe into a second syringe module, putting the second syringe module on standby.

Figure 6B:
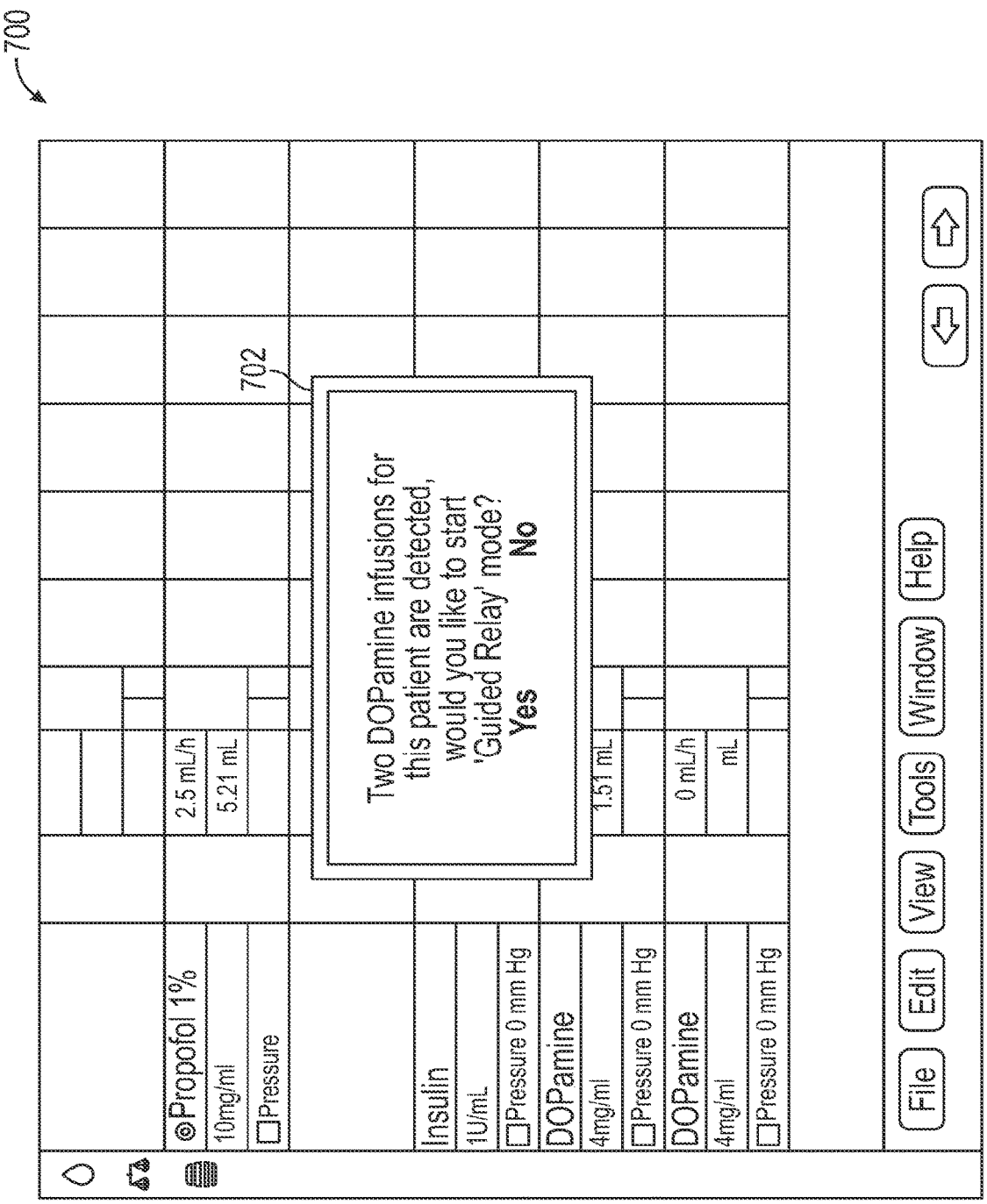

As shown in FIG. 6B, display screen 700 may be modified responsive to detection, by the guided relay system of two infusions of the same medical fluid (e.g., DOPamine) by providing an alert 702 including a visual request for user input (e.g., a visual display of a question such as "Two DOPamine infusions for this patient are detected, would you like to start 'Guided Relay' mode?"). Options for responding such as "Yes" and "No" may also be provided in alert 702 as shown. The user (e.g., a clinician such as a nurse) may provide a user response to the guided relay system by entering, for example, "Yes" (e.g., using a touchscreen input of display 112 or using input/output components 114 such as buttons to enter a response).

Figure 6C:
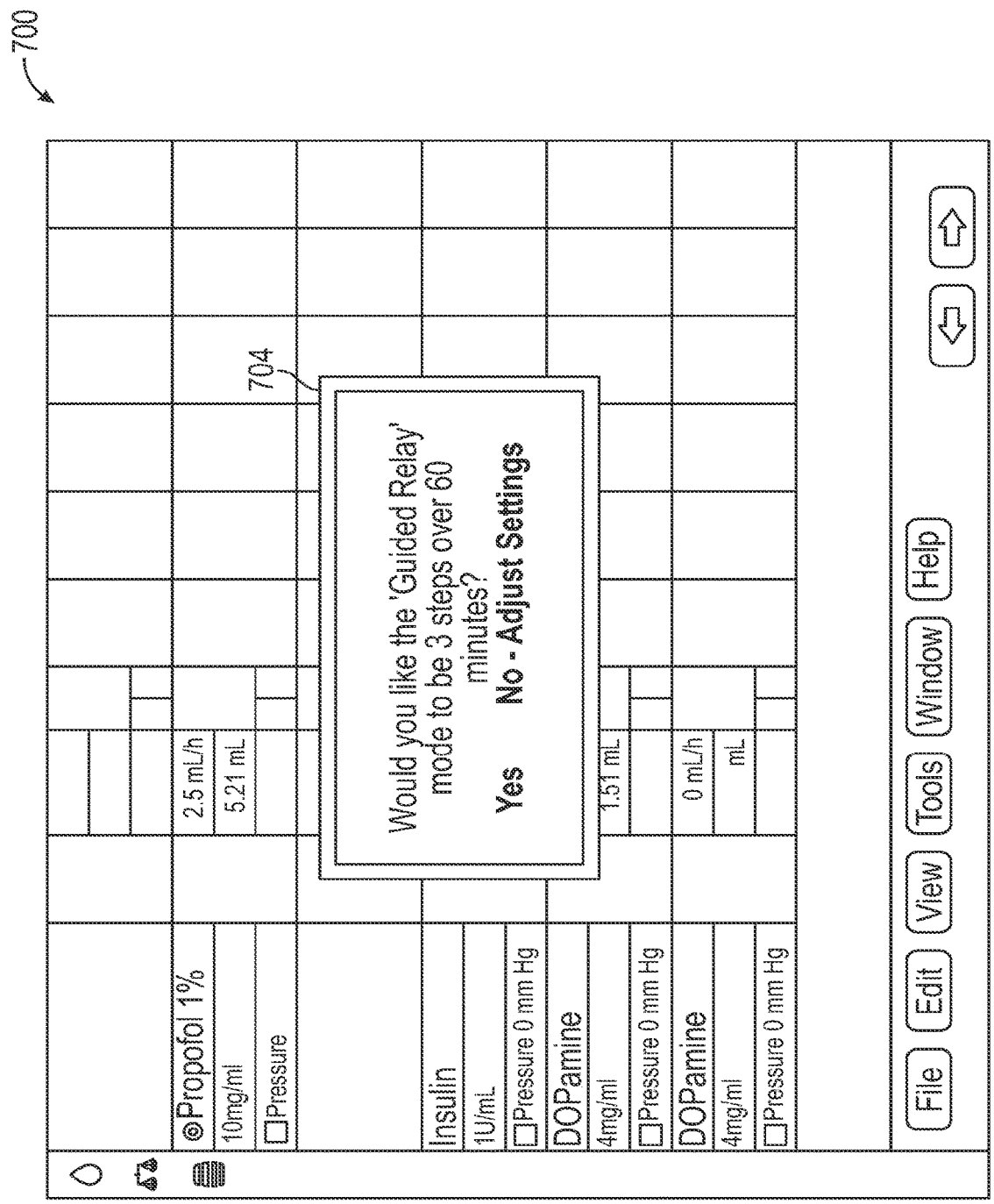

As shown in FIG. 6C, responsive to receiving a "Yes" response to enter the 'Guided Relay' mode, an additional alert 704 may be provided requesting user confirmation or adjustment of the settings of the guided relay. For example, alert 704 may include a visual display of a question such as "Would you like the 'Guided Relay' mode to be 3 steps over 60 minutes?" as shown. Options for responding such as "Yes" and "No—Adjust Settings" may also be provided in alert 704 as shown. The user may enter "Yes" to accept the settings or "No—Adjust Settings" to enter a settings mode in which the user can set the flow rates and/or transition periods for the guided transition.

Figure 6D:
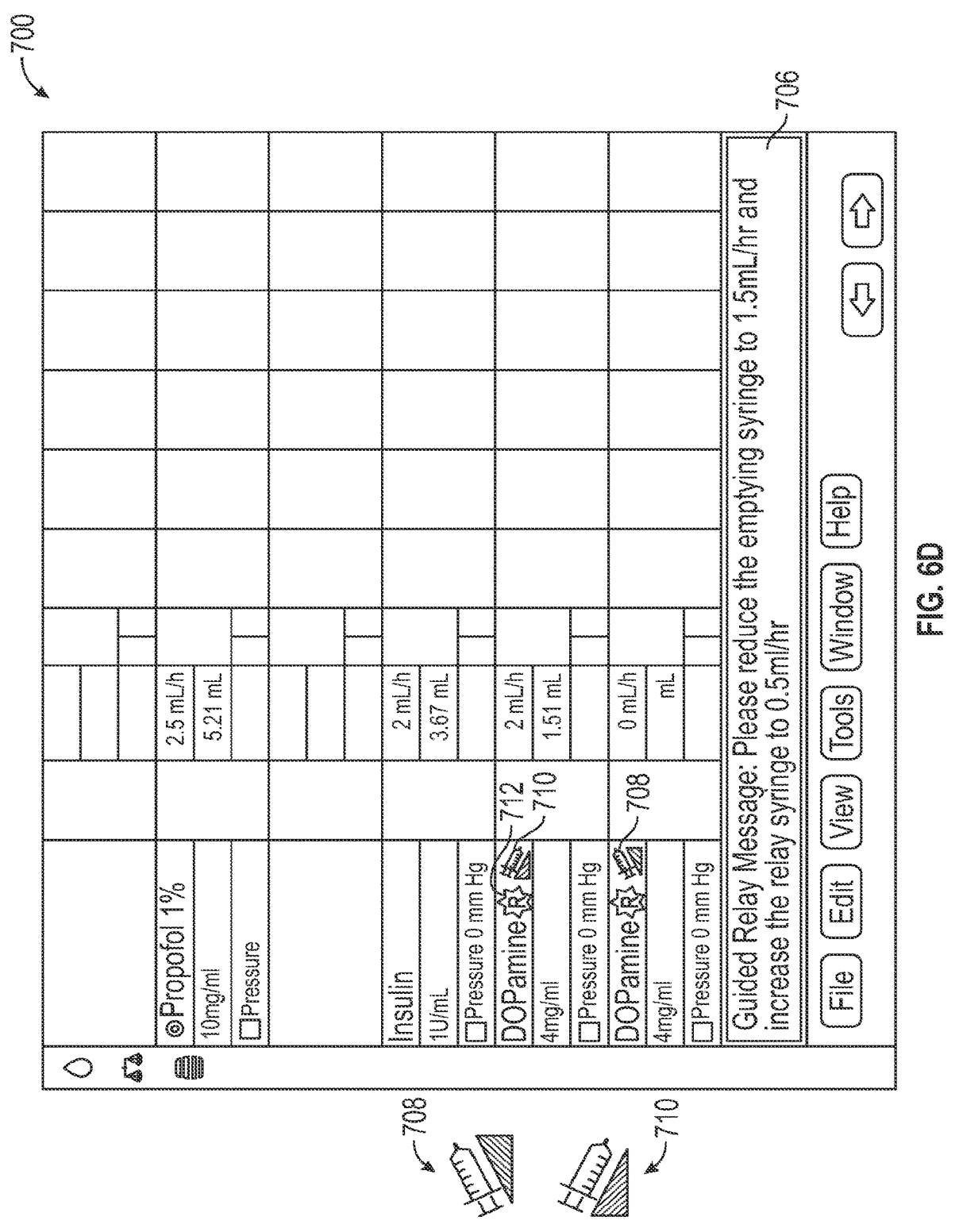

As shown in FIG. 6D, responsive to receiving a "Yes" response to accept the guided relay settings, during a transition period for infusion of the medical fluid from both a first and second syringe, an indicator 708 may be provided that indicates the second or replacement syringe and an indicator 710 may be provided that indicates the first or current syringe. Enlarged versions of indicators 708 and 710 are also shown in FIG. 6D showing how indicators 708 and 710 may be icons that visually identify which syringe has a flow rate that is coming up or down. At a flow rate adjustment time, the guided relay system may provide a visual alert 706 including a message to instruct the clinician to make the first flow rate adjustment (e.g., by reducing a first flow rate of the first syringe and making a corresponding increase of a second flow rate of the second syringe). For example, visual alert 706 may include text such as "Guided Relay Message: Please reduce the emptying syringe to 1.5 mL/hr and increase the relay syringe to 0.5 mL/hr" as shown. An additional icon 712 may be provided for any infusions undergoing guided relay.

As shown in FIG. 6E, a constant message 714 (e.g., a message including text such as "Guided Relay Message: 15 Minutes to Next Rate Change. Next Rate Change will change the emptying syringe to 1 mL and the relay syringe to 1 mL.") may be available counting time to the next rate change window. Message 714 may be displayed, for example, during time period 203 of FIG. 4.

Figure 6F:
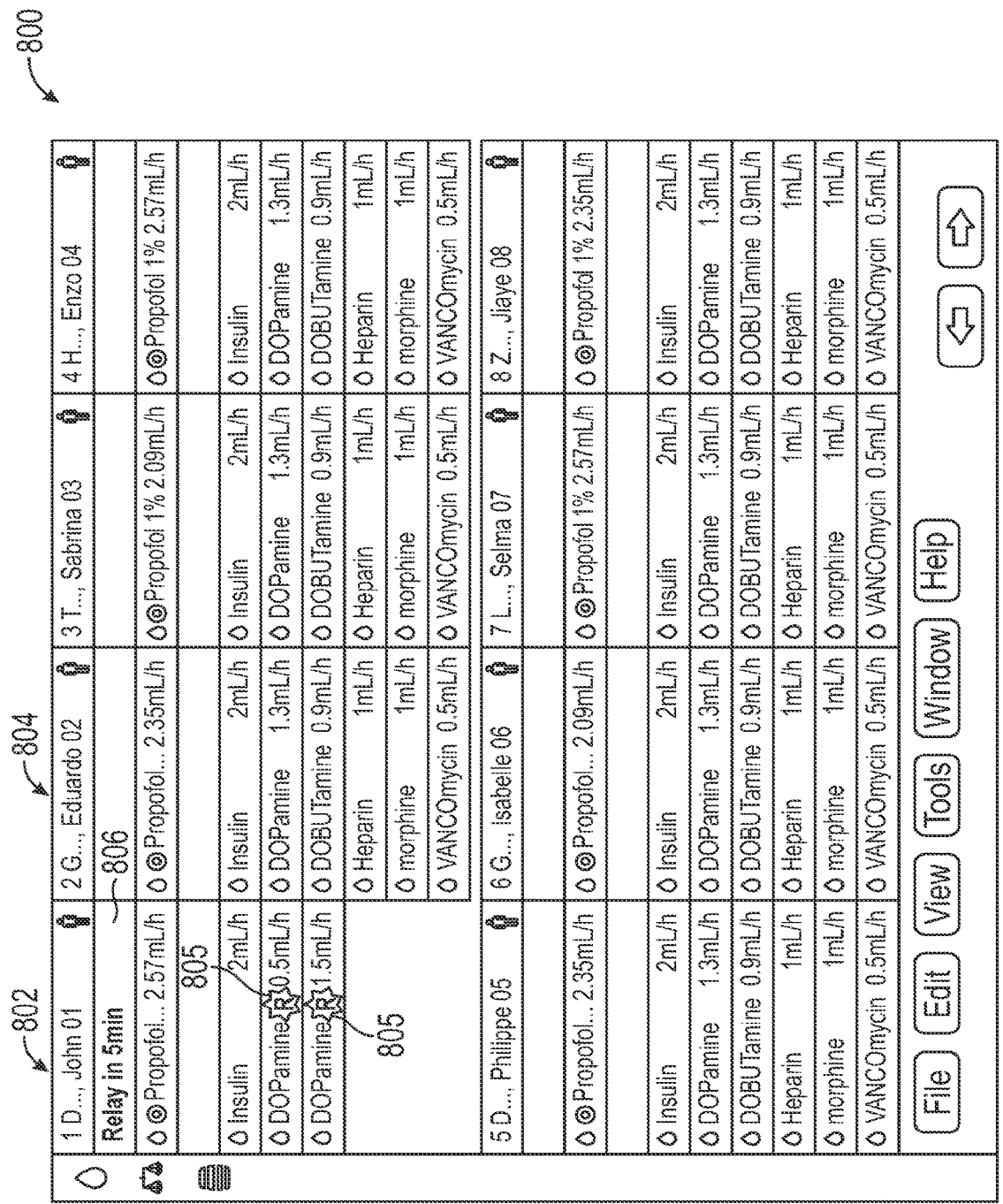

The display screen 700 of FIGS. 6A-6E may be a patient view of a guided relay system that displays infusion information for a particular patient. As shown in FIG. 6F, a guided relay system such as system 100 may also provide a ward view display screen 800 that displays infusion information such as display portions 802 and 804 for multiple patients in a particular ward of a medical care facility. As shown in display portion 802 of ward view 800, the ward view may include an indication 805 of the drugs in guided relay and an information message 806 that includes an amount of time until the next changes in the rates for each syringe.

As shown in FIG. 6G, an additional alert 716 may be provided, during a set time window, to make a rate change. For example, the guided relay system may update display screen 700 to include a message in alert 716 to indicate to the clinician that the rate change is in the time window for the rate change. For example, alert 716 may include text such as "Guided Relay Message: Within window to make a Rate Change. Please change the emptying syringe to 0.5 mL and the relay syringe to 1.5 mL." as shown.

Figure 6H:
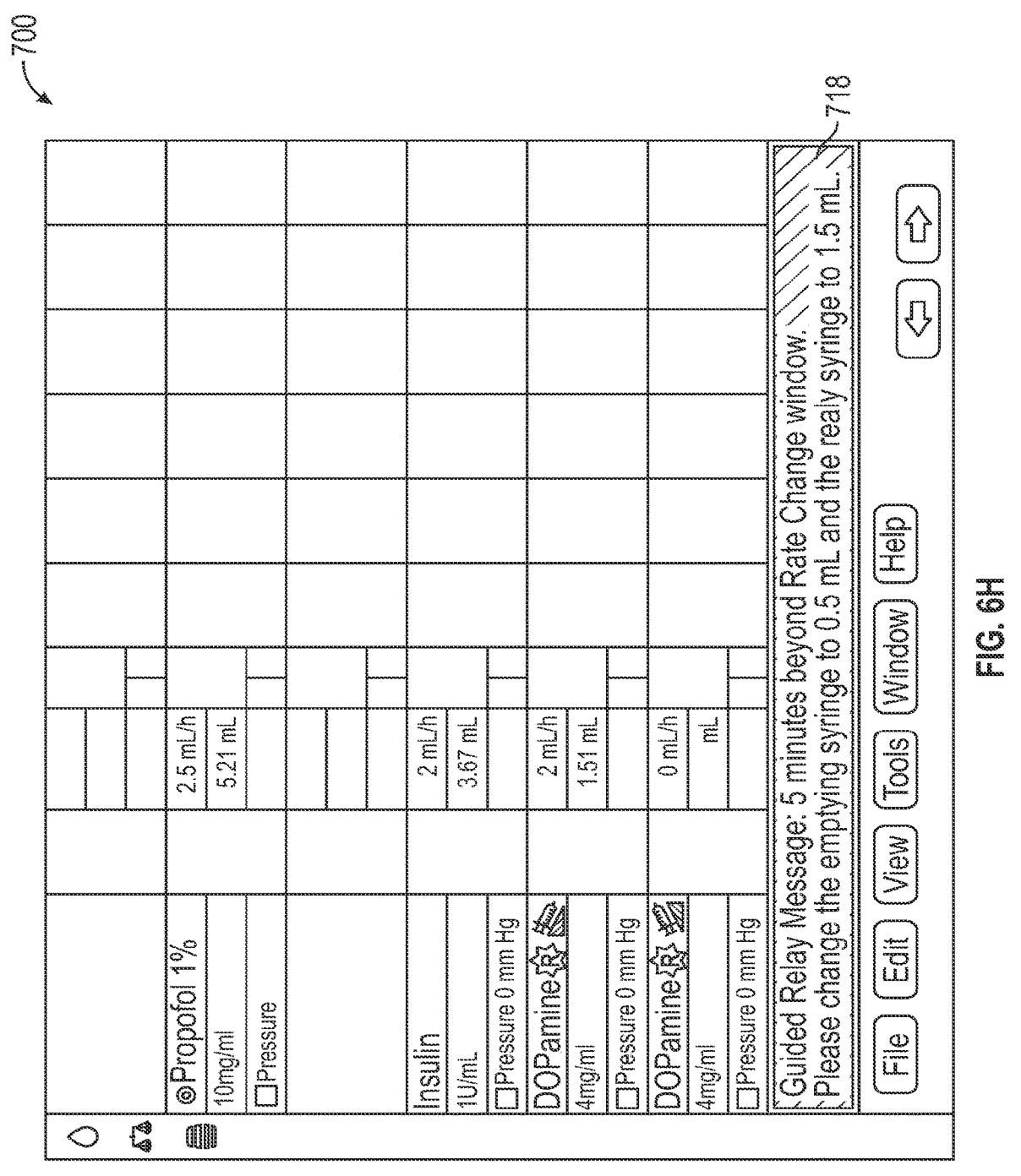

As shown in FIG. 6H, an additional alert 718 may be provided if the scheduled rate change is not made. For example, the guided relay system may update display screen 700 to include a message in alert 718 that includes text such as "Guided Relay Message: 5 minutes beyond Rate Change window. Please change the emptying syringe to 0.5 mL and the relay syringe to 1.5 mL." An audio alarm may also be generated. Alert 718 may be provided in a different color (e.g., red) from other alerts and/or messages (e.g., yellow alerts and/or messages) to indicate a more serious alert or that an error has been or is about to be made.

Figure 6I:
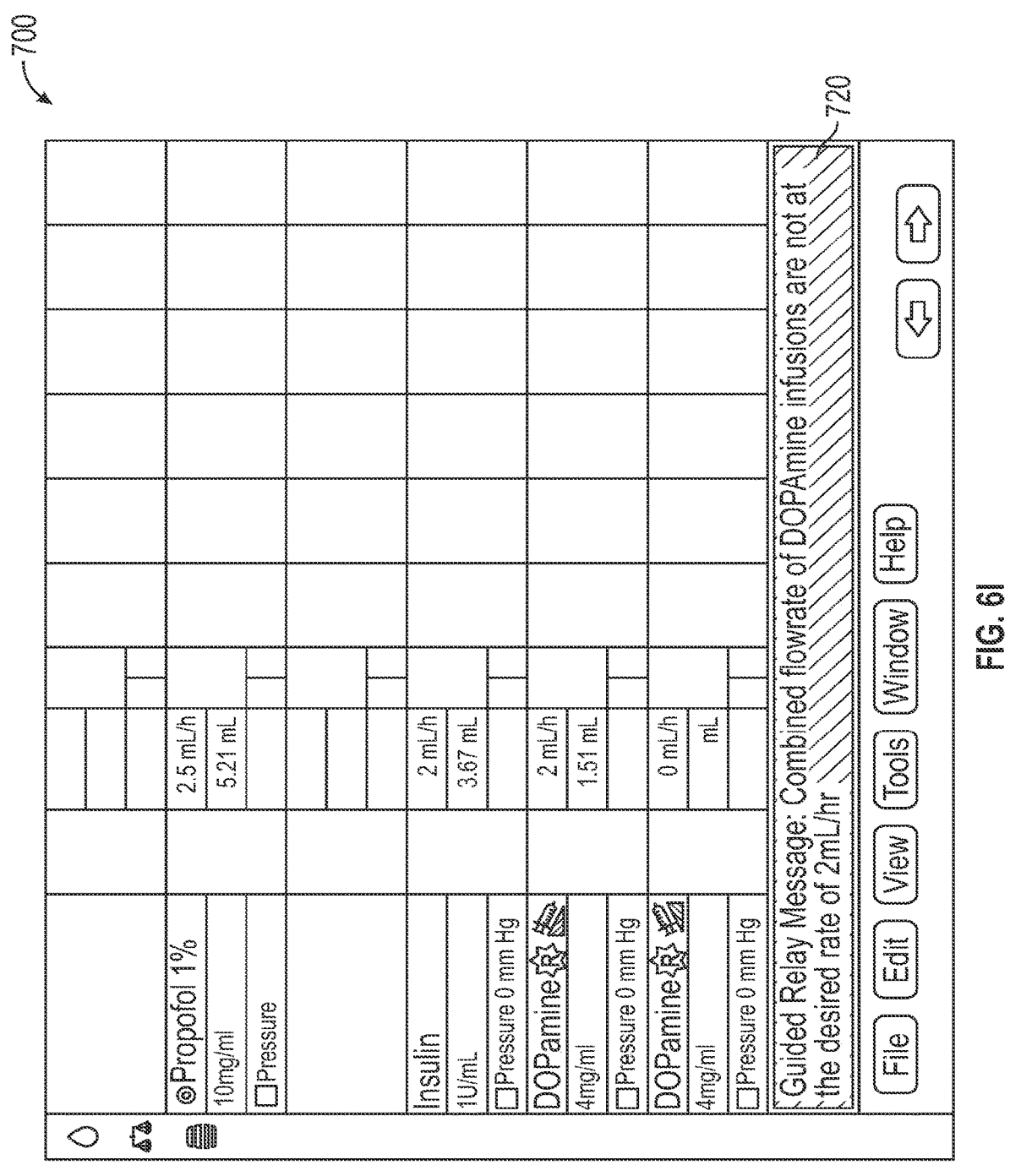

As shown in FIG. 6I, if the combined flow rate between the two DOPamine infusions isn't at the intended combined rate (e.g., 2 mL/hr), an alert 720 may be provided with, for example, text that states "Guided Relay Message: Combined flowrate of DOPamine infusions are not at the desired rate of 2 mL/hr!"

As shown in FIGS. 6J and 6K, following an appropriate adjustment responsive to alert 718 or 720, display screen 720 may be modified to display an alert 722 indicating the time and parameters for the next flow rate change and then an alert 724 indicating that the time window for the next flow rate range change has arrived. Message 722 may be displayed, for example, during time period 205 of FIG. 4.

Figure 6L:
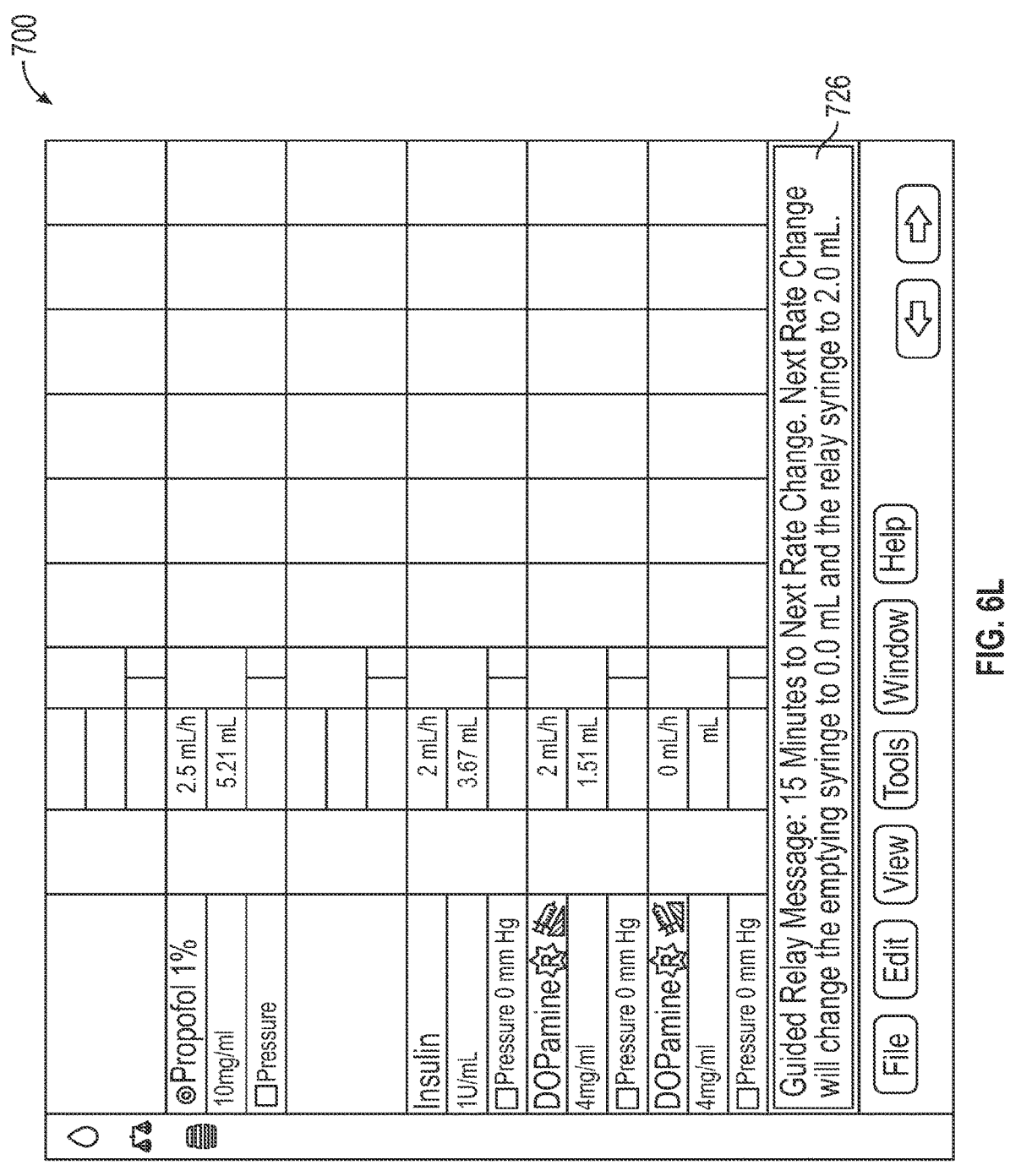

As shown in FIGS. 6L and 6M, following the transition associated with alerts 722 and 724, display screen 720 may be modified to display an alert 726 indicating the time and parameters for the next flow rate change and then an alert 728 indicating that the time window for the next flow rate range change has arrived. Message 726 may be displayed, for example, during time period 207 of FIG. 4.

As shown in FIG. 6N, upon completion of the transition of the guided relay from the first syringe to the second syringe, display screen 700 may be updated to include message 730 requesting a response related to reporting. For example, message 730 may include text such as "'Guided Relay' is complete. Send syringe transition information to PDMS?" as shown. Options for responding such as "Yes" and "No—Keep it Separate" may also be provided in alert 730 as shown. The user may enter "Yes" to transmit syringe transition information to the PDMS or "No—Keep it Separate" to prevent or delay the transmission.

Although the guided relay messages and alerts described herein include examples in which the guided relay messages and alerts include instructions for a clinician to make adjustments, it should be appreciated that the systems and methods described herein may also apply to guided relay messages and alerts that merely inform the clinician that flow rates for a relay transmission from a first syringe to a second syringe (or a first IV bag to a second IV bag) as described herein are being automatically adjusted (e.g., by an infusion pump operating both the first and second syringes).

The subject technology is illustrated, for example, according to various aspects described above. Various examples of these aspects are described as numbered concepts or clauses (1, 2, 3, etc.) for convenience. These concepts or clauses are provided as examples and do not limit the subject technology. It is noted that any of the dependent concepts may be combined in any combination with each other or one or more other independent concepts, to form an independent concept. The following is a non-limiting summary of some concepts presented herein:

Concept 1. A computer-implemented method, comprising:
operating a first syringe to administer a medical fluid to a patient from the first syringe;
detecting a second syringe;
providing one or more guided relay messages to a user for transitioning from administering the medical fluid from the first syringe to administering the medical fluid from the second syringe.

Concept 2. The method of Concept 1 or any other Concept, wherein transitioning from administering the medical fluid from the first syringe to administering the medical fluid from the second syringe comprises, during a transition period, providing the medical fluid to the patient simultaneously from the first syringe and the second syringe for at least a portion of the transition period.

Concept 3. The method of Concept 2 or any other Concept, wherein transitioning from administering the medical fluid from the first syringe to administering the medical fluid from the second syringe further comprises, during the transition period, periodically reducing a first flow rate of the medical fluid to the patient from the first syringe and correspondingly increasing a second flow rate of the medical fluid to the patient from the second syringe.

Concept 4. The method of Concept 3 or any other Concept, wherein providing the one or more guided relay messages comprises providing a first guided relay message that includes instructions to the user to increase the second flow rate of the medical fluid to the patient from the second syringe and reduce the first flow rate of the medical fluid to the patient from the first syringe.

Concept 5. The method of Concept 4 or any other Concept, wherein providing the one or more guided relay messages comprises providing a second guided relay message that includes a time until a next adjustment of the first flow rate and the second flow rate.

Concept 6. The method of Concept 5 or any other Concept, wherein providing the one or more guided relay messages comprises providing a third guided relay message that includes an alert that a scheduled adjustment did not occur.

Concept 7. The method of Concept 5 or any other Concept, wherein providing the one or more guided relay messages comprises providing a third guided relay message that includes an alert that a combined flow rate corresponding to the first flow rate and the second flow rate is not equal to a target flow rate.

Concept 8. The method of Concept 1 or any other Concept, wherein the operating comprises operating the first syringe with a pump.

Concept 9. The method of Concept 1 or any other Concept, wherein the providing comprises providing the one or more guided relay messages using a display of an infusion pump, the display operated by a guided relay system of the infusion pump.

Concept 10. An infusion pump comprising processing circuitry and non-transitory machine-readable media, the non-transitory machine-readable media storing instructions that, when executed by the processing circuitry cause the processing circuitry to:
operate a first syringe that is coupled to the infusion pump to move a medical fluid from the first syringe into infusion tubing;
detect a second syringe coupled to the infusion pump; and
provide one or more guided relay messages on a display of the infusion pump for transitioning from administering the medical fluid from the first syringe to administering the medical fluid from the second syringe.

Concept 11. The infusion pump of Concept 10 or any other Concept, wherein the one or more guided relay messages comprises includes a time until an adjustment of a first flow rate for the first syringe and a corresponding adjustment of a second flow rate for the second syringe.

Concept 12. The infusion pump of Concept 11 or any other Concept, wherein the corresponding adjustment of the second flow rate is equal and opposite to the adjustment of the first flow rate.

Concept 13. The infusion pump of Concept 11 or any other Concept, wherein the one or more guided relay messages comprises an alert that a scheduled adjustment of the first flow rate or the second flow rate did not occur.

Concept 14. The infusion pump of Concept 11 or any other Concept, wherein the one or more guided relay messages comprises an alert that a combined flow rate corresponding to the first flow rate and the second flow rate is not equal to a target flow rate.

Concept 15. A system, comprising:
a first actuable component configured to couple to a plunger of a first syringe containing a medication;
a second actuable component configured to couple to a plunger of a second syringe containing the same medication;
a display; and
a processor configured to:
operate the first actuable component to move the plunger of the first syringe at a first rate;
operate the second actuable component to move the plunger of the second syringe at a second rate while operating the first actuable component at the first rate; and
operate the display to provide a message that describes a decrease in the first rate and a corresponding increase in the second rate.

Concept 16. The system of Concept 15 or any other Concept, wherein the processor is further configured to operate the display to provide a message that describes a further decrease in the first rate and a corresponding further increase in the second rate.

Concept 17. The system of Concept 15 or any other Concept, further comprising infusion lines coupled to the first syringe and the second syringe and at least one flow sensor configured to obtain a measured flow rate of the medication in the infusion lines.

Concept 18. The system of Concept 17 or any other Concept, wherein the processor is further configured to operate the display to generate, based on the measured flow rate, an alert that a scheduled adjustment of the first rate or the second rate did not occur.

Concept 19. The system of Concept 17 or any other Concept, wherein the processor is further configured to operate the display to generate, based on the measured flow rate, an alert that a combined flow rate corresponding to the first rate and the second rate is not equal to a target flow rate.

Concept 20. The system of Concept 15 or any other Concept, wherein the message comprises instructions to decrease the first rate and increase the second rate.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed:

1. A system, comprising:
   a first syringe containing a type of a medication;
   a second syringe containing the type of the medication;
   a display; and
   a processor configured to:
   receive one or more patient vital signs having first monitoring limits during operation of the first syringe only;
   set second monitoring limits of the one or more patient vital signs tighter than the first monitoring limits during a transition period from the operation of the first syringe only to operation of the second syringe only; and
   generate an alert that one of the first monitoring limits or the second monitoring limits have been exceeded.

2. The system of claim 1, further comprising:
   a first actuable component configured to couple to a first syringe plunger; and
   a second actuable component configured to couple to a second syringe plunger.

3. The system of claim 2, wherein the processor is further configured to:
   operate the first actuable component to move the first syringe plunger at a first rate; and
   operate the second actuable component to move the second syringe plunger at a second rate.

4. The system of claim 3, wherein the processor is further configured to provide a message on the display that describes a decrease in the first rate and a corresponding increase in the second rate.

5. The system of claim 3, wherein the processor is further configured to generate an alert that a scheduled adjustment of the first rate or the second rate did not occur.

6. The system of claim 3, wherein the processor is further configured to generate an alert that a combined flow rate corresponding to the first rate and the second rate is not equal to a target flow rate.

7. The system of claim 3, wherein the processor is further configured to provide an icon on the display that visually indicates one of a currently increasing flow rate or a currently decreasing flow rate of the first syringe.

8. The system of claim 3, wherein the processor is further configured to set the second rate as an initial priming rate to prime the second syringe.

9. The system of claim 3, wherein the processor is configured to revert the first actuable component and the second actuable component back to flow rate settings of an immediately preceding step based on exceeding the second monitoring limits of the one or more patient vital signs.

10. The system of claim 1, further comprising:
    a first infusion line coupled to the first syringe;
    a second infusion line coupled to the second syringe; and
    at least one flow sensor configured to obtain a first measured flow rate of the medication in the first infusion line and a second measured flow rate of the medication in the second infusion line.

11. The system of claim 10, wherein the processor is further configured to generate the alert based on one of the first measured flow rate or the second measured flow rate.

12. The system of claim 1, wherein the processor is further configured to display a ward view comprising information for multiple sets of the first syringe and the second syringe.

13. A computer-implemented method, comprising:
    operating a first syringe containing a type of a medical fluid;
    operating a second syringe containing the type of the medical fluid;
    receiving, from one or more vital sign monitors, one or more patient vital signs having first monitoring limits during the operating of the first syringe only;
    setting, by a processor, second monitoring limits of the one or more patient vital signs tighter than the first monitoring limits during a transition period from the operating of the first syringe only to the operating of the second syringe only; and
    generating an alert that one of the first monitoring limits or the second monitoring limits have been exceeded.

14. The method of claim 13, wherein transitioning from administering the medical fluid from the first syringe to administering the medical fluid from the second syringe comprises, during the transition period, providing the medical fluid simultaneously from the first syringe and the second syringe for at least a portion of the transition period.

15. The method of claim 14, wherein the transitioning from the administering the medical fluid from the first syringe to the administering the medical fluid from the second syringe further comprises, during the transition period, periodically reducing a first flow rate of the medical fluid from the first syringe and correspondingly increasing a second flow rate of the medical fluid from the second syringe.

16. The method of claim 15, further comprising providing a guided relay message that includes instructions to increase the second flow rate of the medical fluid from the second syringe and reduce the first flow rate of the medical fluid from the first syringe.

17. The method of claim 15, further comprising providing a guided relay message that includes a time until a next adjustment of one of the first flow rate and the second flow rate.

18. The method of claim 15, further comprising providing a guided relay message that includes an alert that a scheduled adjustment did not occur.

19. The method of claim 15, further comprising providing a guided relay message that includes an alert that a combined flow rate corresponding to the first flow rate and the second flow rate is not equal to a target flow rate.

20. An infusion pump comprising processing circuitry and non-transitory machine-readable media, the non-transitory machine-readable media storing instructions that, when executed by the processing circuitry cause the processing circuitry to:

operate a first syringe that is coupled to the infusion pump to move a medical fluid from the first syringe into infusion tubing;

operate a second syringe that is coupled to the infusion pump to move the medical fluid from the second syringe into the infusion tubing;

receive one or more patient vital signs having first monitoring limits;

set second monitoring limits of the one or more patient vital signs tighter than the first monitoring limits during a transition from administering the medical fluid from the first syringe to administering the medical fluid from the second syringe; and provide an alert that one of the first monitoring limits or the second monitoring limits have been exceeded.

\* \* \* \* \*